United States Patent [19]

Martin

[11] Patent Number: 4,687,861

[45] Date of Patent: Aug. 18, 1987

[54] MICROBICIDAL COMPOSITIONS

[75] Inventor: Pierre Martin, Rheinfelden, Switzerland

[73] Assignee: Ciba-Geigy Corporation, Ardsley, N.Y.

[21] Appl. No.: 800,845

[22] Filed: Nov. 22, 1985

[30] Foreign Application Priority Data

Nov. 28, 1984 [CH] Switzerland .......................... 5677/84

[51] Int. Cl.$^4$ .......................................... C07D 207/22
[52] U.S. Cl. .................................................. 548/565
[58] Field of Search ......................... 514/429; 548/565

[56] References Cited

FOREIGN PATENT DOCUMENTS 1470386 5/1969 Fed. Rep. of Germany ...... 548/565
2927480 1/1980 Fed. Rep. of Germany .

Primary Examiner—Joseph Paul Brust
Attorney, Agent, or Firm—Edward McC. Roberts; Meredith C. Findlay

[57] ABSTRACT

There are described novel microbicides and the production thereof, which correspond to the formula I

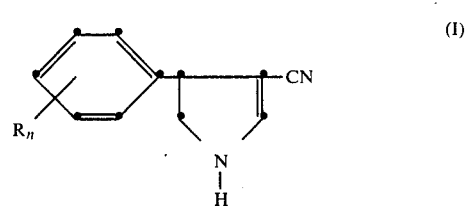

in which R is halogen, $C_1$–$C_6$-alkyl or $C_1$–$C_6$-haloalkyl, and n is 0, 1 or 2. The novel compounds are valuable active substances, particularly for controlling phytopathogenic fungi and bacteria. The compounds are suitable for protecting cultivated plants and seed, and can be advantageously used for the protection of stored stocks and provisions.

5 Claims, No Drawings

MICROBICIDAL COMPOSITIONS

The present invention relates to novel 3-cyano-4-phenylpyrroline derivatives having microbicidal activity, to compositions containing these active substances as active components, and to the use of the active substances or of compositions containing them for controlling harmful microorganisms, particularly phytopathogenic fungi and bacteria. The invention relates also to the production of the novel compounds.

The novel compounds correspond to the general formula I

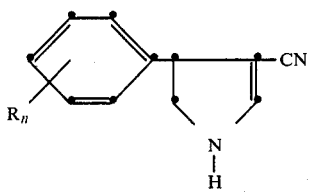

wherein

R is halogen, $C_1$–$C_6$-alkyl or $C_1$–$C_6$-haloalkyl, and n is 0, 1 or 2.

By the term 'alkyl' itself or alkyl as constituent of haloalkyl are meant for example the following straight-chain or branched-chain groups: methyl, ethyl, propyl, butyl, pentyl or hexyl, as well as isomers thereof, for example isopropyl, isobutyl, sec-butyl, tert-butyl, isopentyl, neopentyl and isopentyl.

Halo as a part of the substituent haloalkyl denotes the single or multiple occurrence of fluorine, chlorine, bromine or iodine, preferably fluorine, chlorine or bromine, in the alkyl group. Such halogenated alkyl groups are for example: $CH_2Cl$, $CH_2F$, $CHCl_2$, $CHF_2$, $CH_2CH_2Br$, $C_2Cl_5$, $CH_2Br$ or $CHBrCl$, preferably $CF_3$.

Preferred compounds of the formula I are those in which R is chlorine, bromine or methyl, and n is 1 or 2.

Particularly preferred compounds of the formula I are those in which R is chlorine or methyl, and n is 2.

A preferred individual compound is 3-cyano-4-(2',3'-dichlorophenyl)-$\Delta^2$-pyrroline.

The compounds of the formula I are produced according to the invention by reducing compounds of the formula II

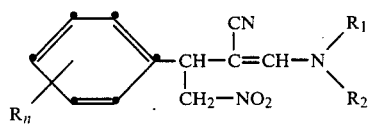

to compounds of the formula III

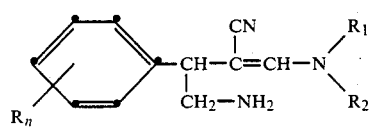

in which $R_1$ and $R_2$ independently of one another are each $C_1$–$C_4$-alkyl, preferably methyl, or together with the adjacent nitrogen atom are pyrrolidinyl or piperidinyl, or with an additional oxygen atom are morpholinyl, and $R_n$ has the meaning defined under the formula I; and subsequently cyclising the products obtained to compounds of the formula I.

The reduction is effected in organic solvents at elevated temperature, under hydrogen pressure, in the presence of a catalyst.

Elevated temperatures and optionally the presence of a weakly acid medium are required for the ring closure reaction.

The reaction medium can be selected from the group comprising the following solvents: aliphatic and aromatic hydrocarbons, for example benzene, toluene, the xylenes or petroleum ether; esters, such as ethyl acetate, propyl acetate or butyl acetate; ethers and ethereal compounds, for example dialkyl ether, such as diethyl ether, diisopropyl ether, tert-butylmethyl ether or, for example, anisole and in particular cyclic ethers, such as dioxane or tetrahydrofuran; and alcohols, for example alkanols, such as methanol and ethanol. Also suitable are mixtures of such solvents.

The process according to the invention is performed at a temperature of between 0° and 150° C. The preferred range for the reduction reaction is between 15° and 110° C. The ring closure reaction is carried out preferably at a temperature of between 50° and 150° C.

The reduction reaction is generally performed by catalytic methods. Catalysts suitable for this purpose are for example platinum, palladium, rhodium, cobalt polysulfide or Raney nickel. Preferred catalysts are those formed from platinum/active charcoal and cobalt polysulfide.

The hydrogen pressures used for the reduction process are in general between 1 and 150 bar initial pressure, measured at room temperature. Hydrogen pressures of between 2 and 120 bar are preferred for the reduction.

It is advantageous in the process described in the foregoing for producing compounds of the formula I when the reduction of the compounds of the formula II and the cyclisation of the reduced compounds of the formula III are carried out in one single reaction step. This reaction procedure constitutes a preferred embodiment of the process according to the invention. The reaction temperatures are in this case between 15° and 150° C.

The compounds of the formula II used as intermediates for the synthesis according to the invention are novel. They are produced by reacting, at elevated temperature and in inert solvents, compounds of the formula IV

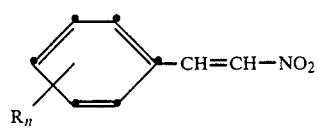

with compounds of the formula V

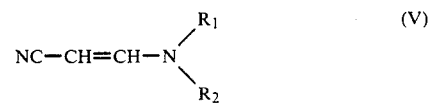

in which $R_1$ and $R_2$ independently of one another are each $C_1$–$C_4$-alkyl, preferably methyl, or together with the adjacent nitrogen atom are pyrrolidinyl or piperidinyl or with an additional O atom are morpholinyl, and R and n have the meanings defined under the formula I.

Suitable solvents are aliphatic and aromatic hydrocarbons, for example benzene, toluene, the xylenes or petroleum ether, preferably toluene; also ethers, such as dioxane or tetrahydrofuran, especially tetrahydrofuran; and also alcohols, for example methanol or ethanol, particularly ethanol. Also applicable are mixtures of such solvents with one another, as well as mixtures of the solvents with water.

The process for producing compounds of the formula II is performed at temperatures of between 0° and 200° C., preferably between 40° and 130° C.

The compound of the formula IV serving as starting material for the reaction described in the foregoing is likewise novel. It can be produced by reacting compounds of the formula VI

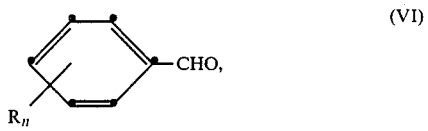

in which R and n have the meanings defined under the formula I, with nitromethane in the presence of ammonium acetate in glacial acetic acid, at a temperature of between 70° and 130° C.

The benzaldehydes of the formula VI are generally known and can be produced by known methods.

The novel compounds of the formula II

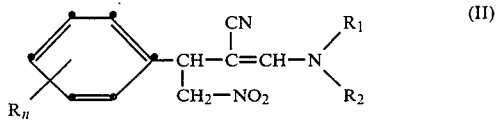

in which $R_1$ and $R_2$ independently of one another are each $C_1$-$C_4$-alkyl, preferably methyl, or together with the adjacent nitrogen atom are pyrrolidinyl or piperidinyl, or with an additional oxygen atom are morpholinyl, are valuable intermediates for the production according to the invention of the novel microbicidally active compounds of the formula I and hence form a part of the present invention.

Further subject matter of the present invention relates to the production of compounds of the formula VII

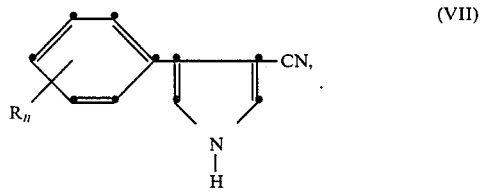

in which $R_n$ has the meanings defined under the formula I, which are obtainable by oxidation of the novel compounds of the formula I. The oxidation process is performed by means of bromine, or in the presence of a catalyst acting as the oxidising medium, in an inert solvent at a temperature of between 0° and 250° C. With the use of bromine, temperatures of 0° to 80° C. are preferred, and with the use of a catalyst the preferred temperatures are 150° to 250° C. The catalysts used are those which are suitable for oxidising reactions (hydrogen transfer), palladium/active charcoal being preferred.

Suitable as catalysts are also polyvalent metal cations. Technically very advantageous cations are $Cu^{++}$ and particularly $Fe^{+++}$. Preferred salts are especially $FeCl_3$ and $FeBr_3$.

In the oxidation process, air or oxygen is passed through the reaction mixture, or is introduced under pressure (e.g. 2 to 120 bar) in an autoclave. Suitable solvents are water or aqueous solvent mixtures with alcohols (methanol, ethanol, isopropanol, and so forth); dioxane or tetrahydrofuran; dimethyl sulfoxide; dimethyl formamide, or other solvents miscible with water. The temperature range for oxidation by air in the presence of metal salts is as a rule 0° to 90° C., preferably 5° to 80° C.

Some compounds of the formula VII are known, for example from the German Offenlegungsschrift No. 2,927,480. It is stated therein that they have phytofungicidal properties.

The novel pyrroline derivatives of the formula I according to the present invention constitute a valuable enlargement of the prior art, for it has been established that the compounds of the formula I surprisingly exhibit a microbicidal spectrum against phytopathogenic fungi and bacteria which is very favourable for agricultural requirements. They not only can be used in arable farming or in similar fields of application for controlling harmful microorganisms on cultivated plants, but can be additionally used, in the protection of stocks, for preserving perishable goods. Compounds of the formula I have very advantageous curative, systemic and in particular preventive properties, and can be used for the protection of numerous, especially arable, crops. The microorganisms occurring on plants or on parts of plants (fruit, blossom, foliage, stalks, tubers or roots) of various cultivated crops can be inhibited or destroyed with the active substances of the formula I, and also parts of plants subsequently growing remain preserved from such microorganisms.

The active substances are effective for example against the phytopathogenic fungi belonging to the following classes: Ascomycetes, for example Erysiphe, Sclerotinia, Fusarium, Monilinia and Helminthosporium; Basidiomycetes, for example Puccinia, Tilletia and Rhizoconia; and also against the Oomycetes belonging to the Phytomycetes class, such as Phytophthora. As plant protective agents, the compounds of the formula I can be applied with a particularly high degree of success against important harmful fungi from the Fungi imperfecti family, for example against Cercospora or Piricularia, and especially against Botrytis. Botrytis spp. (*B. cinera, B. allii*) constitute with botrytis disease on grapevines, strawberries, apples, onions and other fruit and vegetable varieties a significant economic loss factor. Furthermore, some compounds of the formula I can be successfully used for protecting perishable goods of vegetable or animal origin. They combat mould fungi, such as Penicillium, Aspergillus, Rhizopus, Fusarium, Helminthosporium, Nigrospora and Alternaria, as well as bacteria, such as butyric acid bacteria, and yeasts, such as Candida.

As plant protective agents, the compounds of the formula I exhibit, for practical application in agriculture, a very favourable spectrum of activity for protecting cultivated plants, without disadvantageously affecting these by undesirable side effects.

The compounds can also be used as dressing agents for the treatment of seed (fruits, tubers or grain), and of plant cuttings to protect them from fungus infections, and also against phytopathogenic fungi occurring in the soil.

The invention thus relates also to microbicidal compositions, and to the use of the compounds of the formula I for controlling phytopathogenic microorganisms, especially fungi which damage plants, and for preventing an infestation on plants and on provisions of vegetable or animal origin.

In addition, the present invention embraces also the production of agrochemical compositions, whereby the active ingredient is intimately mixed with one or more substances or groups of substances described herein. Also included is a process for treating plants or stored provisions, which process comprises the application of the compounds of the formula I, or of the novel compositions, to the plants or parts of plants, or to the locus or the substrate thereof.

Within the scope of this invention, target crops for plant protection are for example the following varieties of plants: cereals (wheat, barley, rye, oats, rice, sorghum and related cereals); beet (sugar beet and fodder beet); pomaceous fruit, stone fruit and soft fruit (applies, pears, plums, peaches, almonds, cherries, strawberries, raspberries and blackberries); legumes (beans, lentils, peas and soya-beans); oil plants (rape, mustard, poppy, olives, sunflowers, coco, castor-oil plants, cocoa and groundnuts); Curcurbitacea (pumpkins, cucumbers and melons); fibre plants (cotton, flax, hemp and jute); citrus fruits (oranges, lemons, grapefruit and mandarins); varieties of vegetables (spinach, lettuce, asparagus, varieties of cabbage, carrots, onions, tomatoes, potatoes and paprika); laurel plants (avocada, cinnamon and camphor); or plants such as maize, tobacco, nuts, coffee, sugar cane, tea, grapevines, hops, bananas and natural rubber plants; and also ornamental plants (composites).

As protective agents for stored products, the compounds of the formula I are used either in an unmodified form or preferably together with auxiliaries customarily employed in formulation practice, and are thus processed, in a known manner, for example into the form of emulsion concentrates, brushable pastes, directly sprayable or dilutable solutions, diluted emulsions, wettable powders, soluble powders, dusts or granulates, and also encapsulations in for example polymeric substances. The application processes, such as spraying, scattering, brushing or pouring, and likewise the type of composition, are selected to suit the objectives to be achieved and the prevailing conditions. Favourable applied amounts are in general 0.01 to at most 2 kg of active ingredient per 100 kg of substrate to be protected; the amounts depend however quite considerably on the nature (extent of surface area, consistency, and moisture content) of the substrate and on environmental influences thereon.

Within the scope of the present invention, stored stocks and provisions are vegetable and/or animal natural materials and products from further processing, for example the plants which are listed in the following and which have been taken out from the natural life cycle, and parts of these plants (stalks, leaves, tubers, seeds, fruits and grains), the materials being in the freshly harvested condition or in the form resulting from further processing (pre-dried, moistened, crushed, ground or roasted). The following productive materials may be given as examples, which however have no limiting character with respect to the scope of this invention: cereals (such as wheat, barley, rye, oats, rice, sorghum and related cereals); beet (such as carrots, sugar beet and fodder beet); pomaceous fruit, stone fruit and soft fruit (such as apples, pears, plums, peaches, almonds, cherries, strawberries, raspberries and blackberries); legumes (such as beans, lentils, peas and soya-bean); oil plants (such as rape, mustard, poppy, olives, sunflowers, coco, castor-oil plants, cocoa and groundnuts); Cucurbitacea (such as pumpkins, cucumbers and melons); fibre plants (such as cotton, flax, hemp, jute and nettles); citrus fruits; varieties of vegetables (such as spinach, lettuce, asparagus and varieties of cabbage, onions, tomatoes, potatoes and paprika); laurel plants (such as avocada, cinnamon and camphor); or plants such as maize, tobacco, nuts, coffee, sugar cane, tea, grapevines, chestnuts, hops, bananas, grass and hay.

Natural products of animal origin which may be mentioned are in particular dried processed meat and fish products, such as dried meat, dried fish, meat concentrates, bone meal, fish meal and dried animal feed.

By treatment with compounds of the formula I, the treated stored products are lastingly protected against infestation by mould fungi and other undesirable microorganisms. Consequently, the formation of toxic and in part carcinogenic mould fungi (aflatoxines and ochratoxines) is prevented, the material is kept from decomposing, and the quality thereof is maintained high for a prolonged period of time. The process according to the invention can be applied to all dry and moist provisions and stored goods which are susceptible to microorganisms, such as yeasts, bacteria and especially mould fungi.

A preferred process for applying the active substance comprises spraying or wetting the substrate with a liquid preparation, or mixing the substrate with a solid preparation of the active substance. The described conservation process forms a part of the present invention.

Active substances of the formula I are customarily used in the form of compositions, and can be applied, simultaneously or successively, with further active substances to the area or plants to be treated. These further active substances can be fertilisers, trace-element agents or other preparations influencing plant growth. They can however also be selective herbicides, insecticides, fungicides, bactericides, nematicides or molluscicides, or mixtures of several of these preparations, optionally together with carriers commonly used in formulation practice, tensides or other additives facilitating application.

Suitable carriers and additives can be solid or liquid and they correspond to the substances customarily employed in formulation practice, for example: natural or regenerated mineral substances, solvents, dispersing agents, wetting agents, adhesives, thickeners, binders or fertilisers.

A preferred method of applying an active substance of the formula I, or an agrochemical composition containing at least one of these active substances, is application to the foliage (leaf application). The number of applications and the amounts applied are governed by the extent of infestation with respect to the pathogen (fungus genus) concerned. The active substances of the formula I can however be fed into the plant through the soil and then by way of the root system (systemic action), this being achieved by the locus of the plant being soaked with a liquid preparation, or by the substances being introduced in solid form into the soil, for example in the form of a granulate (soil application). The compounds of the formula I can also be applied to the seed grains (coating), the grains being for this purpose either soaked with a liquid preparation of the active substance or coated with a solid preparation. Further forms of application are possible in special cases, for example the specific treatment of the stalks or buds of the plants.

The compounds of the formula I are used either in an unmodified form or preferably together with auxiliaries customarily employed in formulation practice, and are thus processed, in a known manner, for example into the form of emulsion concentrates, brushable pastes, directly sprayable or dilutable solutions, diluted emulsions, wettable powders, soluble powders, dusts or granulates, and also encapsulations in for example polymeric substances. The application processes, such as spraying, atomising, dusting, scattering, brushing or pouring, and likewise the type of composition, are selected to suit the objectives to be achieved and the given conditions. Favourable applied amounts are in general between 50 g and 5 kg of active substance (AS) per hectare, preferably between 100 g and 2 kg of AS per hectare, and in particular between 200 g and 600 g of AS per hectare.

The formulations, that is to say, the compositions or preparations containing the active substance of the formula I and optionally a solid or liquid additive, are produced in a known manner, for example by the intimate mixing and/or grinding of the active ingredient with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is possible to also add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Particularly advantageous additives facilitating application and rendering possible a marked reduction in the amount of active substance applied are moreover natural (animal or vegetable) or synthetic phospholipides from the class comprising the cephalins and lecithins, for example phosphatidylethanolamine, phosphatidylserine, phosphatidyl glycerol, lysolecithin, plasmalogenes or cardiolipin, which can be obtained for example from animal or plant cells, especially from the brain, heart, liver, egg yokes or soya beans. Applicable commercial mixtures are for example phosphatidylcholine mixtures. Synthetic phospholipides are for example dioctanoyl- phosphatidylcholine and dipalmitoylphosphatidylcholine.

Depending on the nature of the active ingredient of the formula I to be formulated, suitable surface-active compounds are nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are for example the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group being 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkyl-phenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylene-sorbitan-trioleate.

In the case of the cationic tensides, they are in particular quaternary ammonium salts which contain as N-substituents at least one alkyl group having 8 to 22 carbon atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)-ethylammonium bromide. In the storage sector, the additives which are preferred are those that are safe for human and animal foodstuffs.

The tensides customarily used in formulation practice are described, inter alia, in the following publications:

"Mc Cutcheon's Detergents and Emulsifiers Annual" MC Publishing Corp., Ridgewood, N.J., 1981; and Dr. Helmut Stache "Tensid-Taschenbuch" (Tenside Handbook), Carl Hanser Verlag, Munich/Vienna, 1981.

The agrochemical preparations contain as a rule 0.1 to 99%, particularly 0.1 to 95%, of active ingredient of the formula I, 99.9 to 1%, especially 99.8 to 5%, of a solid or liquid additive, and 0 to 25%, in particular 0.1 to 25%, of a tenside.

Whereas commercial products are preferably in the form of concentrated compositions, the preparations employed by the end-user are as a rule diluted.

The compositions can contain further additives, such as stabilizers, antifoaming agents, viscosity regulators, binders and adhesives, as well as fertilisers or other active ingredients for obtaining special effects.

Agrochemical compositions of the types described herein likewise form part of the present invention.

The following Examples serve to further illustrate the invention without limiting the scope thereof.

PRODUCTION EXAMPLES

Example 1

Production of 1-(2',3'-dichlorophenyl)-2-nitroethylene

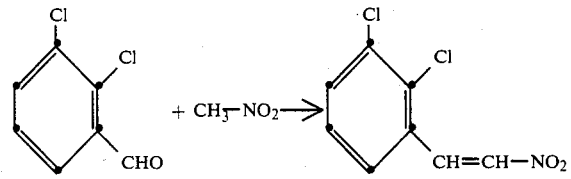

28.0 g of 2,3-dichlorobenzaldehyde, 13.9 g of ammonium acetate, 13.9 ml of nitromethane and 120 ml of glacial acetic acid are refluxed for 2 hours. After cooling, the reaction mixture is poured onto ice and stirred for 30 minutes. The formed precipitate is then filtered off, washed with water and dried in vacuo to thus obtain the product in the form of slightly yellowish crystals, m.p. 89°–91° C. IR (CHCl$_3$) in cm$^{-1}$: 1650 (C=C); 1530 and 1350 (NO$_2$). NMR (CDCl$_3$) in ppm: 7.2–7.7 (m, 4H); 8.50 (d, J=15 Hz, 1H).

Example 2

Production of 1-dimethylamino-2-cyano-3-(2',3'-dichlorophenyl)-5-nitro-but-1-ene

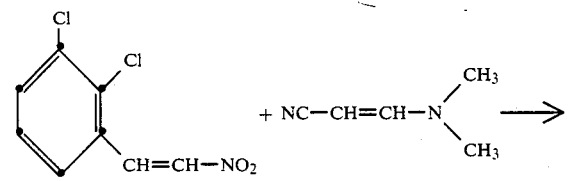

-continued

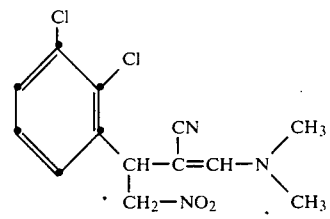

A solution of 109 g of 1-(2',3'-dichlorophenyl)-2-nitroethylene, 49 g of 1-cyano-2-dimethylamino-ethylene and 1.0 liter of abs. toluene are refluxed for 50 hours. After the reaction mixture has cooled, the toluene is evaporated off and the residue obtained is stirred up with diethyl ether. The precipitate is subsequently filtered off, and afterwards washed with a small amount of diethyl ether to thus obtain the product in the form of beige-coloured crystals, m.p. 114°–115° C. IR (CHCl$_3$) in cm$^{-1}$: 2180 (CN), 1635 (C=C), 1555 (NO$_2$). NMR (CDCl$_3$) in ppm: 3.08 (s, 6H); 4.6–5.0 (ABX, 3H); 6.60 (s, 1H); 7.2–7.45 (ABX, 3H).

Example 3

Production of 1-morpholino-2-cyano-3-(2',3'-dichlorophenyl)-4-nitro-but-1-ene 5.0 g of 1-(2',3'-dichlorophenyl)-2-nitroethylene, 3.18 g of 3-morpholinoacrylonitrile and 30 ml of tetrahydrofuran (abs.) are refluxed for 24 hours, and the reaction solution is subsequently concentrated by evaporation. The resulting residue, dissolved in toluene/ethyl acetate (2:1 V/V), is chromatographed through silica gel, and from the eluate is thus obtained the finished product, m.p. 74°–77° C. IR (CHCl$_3$) in cm$^{-1}$; 2200 (CN), 1630 (C=C), 1560 (NO$_2$). NMR (CDCl$_3$) in ppm: 4.5 (m, 4H); 4.7 (m, 4H); 4.8 (ABX, 3H); 6.60 (s, 1H); 7.2–7.5 (m, 3H).

Example 4

Production of 3-cyano-4-(2',3'-dichlorophenyl)-Δ²-pyrroline

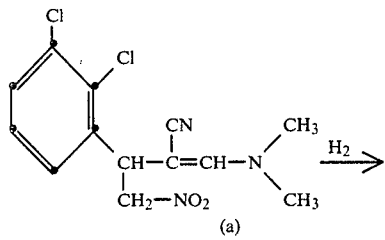

(a)

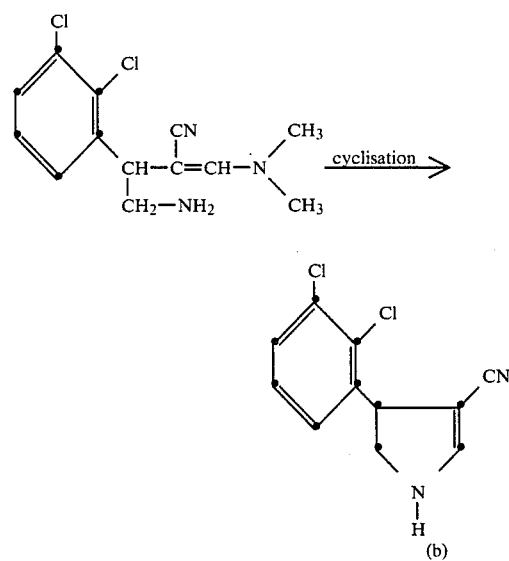

(a) 6.28 g of 1-dimethylamino-2-cyano-3-(2',3'-dichlorophenyl)-4-nitrobut-1-ene are hydrogenated in 100 ml of ethyl acetate at 35° C. and under 4 bar, in the presence of 1.2 g of a platinum/active charcoal catalyst (5%) until the absorption of hydrogen has ceased (=1313 ml of H₂, corresponding to 98% of theory). The mixture is subsequently filtered off from the catalyst, and the solution obtained is concentrated by evaporation.

(b) The residue of (a) is taken up in 45 ml of glacial acetic acid, and the solution is stirred at 50° C. for 1 hour; it is subsequently concentrated by evaporation, and the residue is distributed between ethyl acetate and water; the organic phase is dried over MgSO₄ and then concentrated by evaporation. The residue obtained slowly crystallises and is treated with diethyl ether. The resulting product is in the form of a white powder, m.p. 150°–151° C. IR (CHCl₃) in cm⁻¹: 3450 (NH), 2200 (CN), 1605 (C=C). NMR (CDCl₃) in ppm: 3.4 (dxq, 1H); 4.2 (m, 2H, of which 1H is replaceable by means of D₂O); 4.8 (q, 1H); 7.2–7.4 (m, 4H). MG: 238.

Example 5

Production of 3-cyano-4-(2',3'-dichlorophenyl)-Δ²-pyrroline

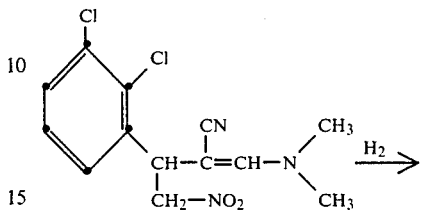

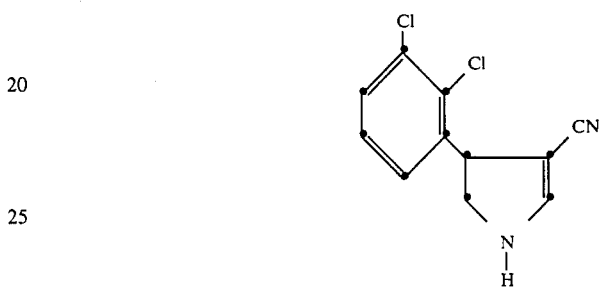

31.4 g of 1-dimethylamino-2-cyano-3-(2',3'-dichlorophenyl)-4-nitrobut-1-ene are hydrogenated in 400 ml of dioxane at 100° C. and 100 bar initial pressure of hydrogen, in the presence of 6.2 g of cobalt polysulfide, for 7½ hours. After this period of time, the measurement at room temperature indicates a hydrogen absorption of 6.39 liters of H₂ (corresponding to 95% of theory). The mixture is subsequently filtered; the catalyst is washed with dioxane and the filtrate is concentrated by evaporation. The residue is chromatographed with toluene/ethyl acetate (2:1) through silica gel to thus obtain the product in the form of a white powder, m.p. 150° C. IR (CHCl₃) in cm⁻¹: 3450 (NH), 2200 (CN), 1605 (C=C). NMR (CDCl₃) in ppm: 3.4 (dxq, 1H); 4.2 (m, 2H, of which 1H is replaceable by means of D₂O); 4.8 (q, 1H); 7.2–7.4 (m, 4H). MG: 238.

Example 6

Production of 3-cyano-4-(2',3'-dichloropheny)-pyrrole

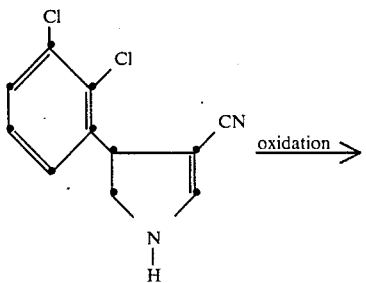

-continued

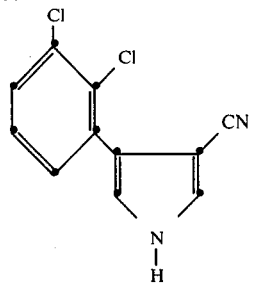

(a) 1.0 g of 3-cyano-4-(2′,3′-dichlorophenyl)-Δ²-pyrroline is dissolved in 15 ml of CHCl₃, and to the solution is added 0.67 g of bromine. After 15 minutes, no further educt is detectable by thin-layer chromatography. 1.4 ml of triethylamine are added to the reaction solution, and stirring is maintained for 1 hour at 40° C. The reaction mixture is subsequently washed with water; the organic phase is then dried over MgSO₄ and concentrated by evaporation. The residue dissolved in toluene-/ethyl acetate (4:1 V/V) is chromatographed through silica gel, and from the eluate is obtained the finished product, m.p. 148°–150° C.

(b) 5.2 g of 3-cyano-4-(2′,3′-dichlorophenyl)-Δ²-pyrroline are stirred in 100 ml of mesitylene, in the presence of 0.5 g of a palladium/active charcoal catalyst, for 14 hours at 180°–200° C. The catalyst is subsequently filtered off and the filtrate is concentrated by evaporation. The residue dissolved in toluene/ethyl acetate (4:1 V/V) is chromatographed through silica gel, and from the eluate is obtained the finished product, m.p. 149°–151° C.

(c) 0.5 g of 3-cyano-4-(2′,3′-dichlorophenyl)-Δ²-pyrroline is stirred with 1.0 g of FeCl₃ in a mixture of 12 ml of water/ethanol (3:1) for 24 hours at room temperature with the introduction of air. The reaction mixture is poured into water and extracted three times with 10 ml of ethyl acetate each time. The organic phase is washed with water, dried over MgSO₄ and concentrated by evaporation. The residue is crystallised by trituration with diethyl ether, and the resulting product is in the form of beige-coloured crystals, m.p. 150°–151° C.

It is shown by the individual reaction steps of the production process according to the invention that the substituent $R_n$ in the phenyl nucleus has negligible effect on the course of the reaction. There can be produced in the same manner for example also the following compounds, which can be used as fungicides:
-3-cyano-4-(2-chlorophenyl)-Δ²-pyrroline,
-3-cyano-4-(2,5-dichlorophenyl)-Δ²-pyrroline,
-3-cyano-4-(2-trifluorophenyl)-Δ²-pyrroline,
-3-cyano-4-(2-bromophenyl)-Δ²-pyrroline,
-3-cyano-4-(3-bromophenyl)-Δ²-pyrroline,
-3-cyano-4-(3-fluorophenyl)-Δ²-pyrroline,
-3-cyano-4-(3-tolyl)-Δ²-pyrroline,
-3-cyano-4-(4-chlorophenyl)-Δ²-pyrroline,
-3-cyano-4-(3-chlorophenyl)-Δ²-pyrroline,
-3-cyano-4-(4-bromophenyl)-Δ²-pyrroline,
-3-cyano-4-(4-fluorophenyl)-Δ²-pyrroline,
-3-cyano-4-(4-tolyl)-Δ²-pyrroline, and
-3-cyano-4-(2,4-dichlorophenyl)-Δ²-pyrroline.

There can be produced by oxidation from such compounds of the formula I corresponding pyrrole derivatives of the formula VII.

FORMULATION EXAMPLES FOR ACTIVE INGREDIENTS OF THE FORMULA I (%=PERCENT BY WEIGHT)

1. Emulsion Concentrates

|  | (a) | (b) | (c) |
|---|---|---|---|
| active ingredient from Examples 4/5 or from the preceding Table | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenyl-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

2. Solutions

|  | (a) | (b) | (c) | (d) |
|---|---|---|---|---|
| active ingredient from Examples 4/5 or from the preceding Table | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

(M.W. = molecular weight)

The solutions are suitable for application in the form of very fine drops.

3. Granulates

|  | (a) | (b) |
|---|---|---|
| active ingredient from Examples 4/5 or from the preceding Table | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

4. Dusts

|  | (a) | (b) |
|---|---|---|
| active ingredient from Examples 4/5 or from the preceding Table | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

5. Wettable Powders

|  | (a) | (b) | (c) |
|---|---|---|---|
| active ingredient from Examples 4/5 or from the preceding Table | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |

-continued

|  | (a) | (b) | (c) |
|---|---|---|---|
| octylphenolpolyethylene glycol ether (7-8 mols of ethylene oxide) | — | 2% | — |
| highly dispersed silicic acid | 5% | 10% | 10% |
| kaolin | 62% | 27% | — |

The active ingredient is well mixed with the additives, and the mixture is thoroughly ground in a suitable mill. Wettable powders which can be diluted with water to give suspensions of the required concentration are obtained.

6. Emulsion Concentrate

| active ingredient from Examples 4/5 or from the preceding Table | 10% |
|---|---|
| octylphenol polyethylene glycol ether (4-5 mols of ethylene oxide) | 3% |
| calcium dodecylbenzenesulfonate | 3% |
| castor oil polyglycol ether (35 mols of ethylene oxide) | 4% |
| cyclohexanone | 30% |
| xylene mixture | 50% |

Emulsions of the required concentration can be obtained from this concentrate by dilution with water.

7. Dusts

|  | (a) | (b) |
|---|---|---|
| active ingredient from Examples 4/5 or from the preceding Table | 5% | 8% |
| talcum | 95% | — |
| kaolin | — | 92% |

Dusts ready for use are obtained by mixing the active ingredient with the carriers and grinding the mixture in a suitable mill.

8. Extruder Granulate

| active ingredient from Examples 4/5 or from the preceding Table | 10% |
|---|---|
| sodium lignin sulfonate | 2% |
| carboxymethylcellulose | 1% |
| kaolin | 87% |

The active ingredient is mixed and ground with the additives, and the mixture is moistened with water. This mixture is extruded and subsequently dried in a stream of air.

9. Coated Granulate

| active ingredient from Examples 4/5 or from the preceding Table | 3% |
|---|---|
| polyethylene glycol (M.W. 200) | 3% |
| kaolin | 94% |

(M.W. = molecular weight)

The finely ground active ingredient is evenly applied in a mixer to the kaolin moistened with polyethylene glycol. Dustfree coated granules are obtained in this manner.

10. Suspension Concentrate

| active ingredient from Examples 4/5 or from the preceding Table | 40% |
|---|---|
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |

The finely ground active ingredient is intimately mixed with the additives. There is thus obtained a suspension concentrate from which can be produced, by dilution with water, suspensions of the concentration required.

BIOLOGICAL EXAMPLES

Example 1

Action Against *Botrytis cinerea* on Bean Plants

Residual-Protective Action

Bean plants about 10 cm in height are sprayed with a spray liquor prepared from wettable powder of the active ingredient (0.002% of active ingredient). The plants are infested after 48 hours with a conidiospore suspension of the fungus. The extent of fungus infection is assessed after incubation of the infested plants for 3 days at 21° C. with 95-100% relative humidity.

The compounds from the Tables greatly reduce fungus infection not only in the above model test but also in the field test. At a concentration of 0.002%, the compound of Examples 4/5 for example proves fully effective (infection 0 to 5%). Infection on infested but untreated bean plants is however 100%.

Example 2

Action Against *Botrytis cinerea* on Apples

Artificially damaged apples are treated by applying drops of spray liquor, prepared from wettable powder of the active ingredient (0.002% of active ingredient), to the damaged areas on the apples. The treated fruit is then inoculated with a spore suspension of *Botrytis cinerea*, and is incubated for one week at about 20° C. with high relative humidity.

For an assessment of the results, the decayed areas of damage are counted, and from the number is deduced the fungicidal action of the test substance. Amongst other effective compounds, the compound of Examples 4/5 completely prevents fungus infection, whereas the level of infection on untreated control fruit is 100%.

What is claimed is:

1. A process for producing a compound of the formula

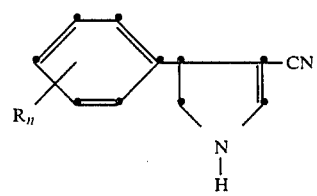

wherein
R is halogen, C1-C6-alkyl or C1-C6-haloalkyl, and
n is 0, 1 or 2, which process comprises reacting with hydrogen a compound of the formula

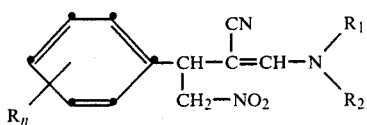

wherein

R1 and R2 independently of one another are each C1-C4-alkyl, or together with the adjacent nitrogen atom are pyrrolidinyl or piperidinyl, or with an additional oxygen atom are morpholinyl, under a nitrogen pressure of 1 to 150 bar, in the presence of a catalyst suitable for catalyzing hydrogen reduction, at a temperature of between 0 and 150 degrees Centigrade and in an organic solvent or solvent mixture; and optionally completing the reaction in a weakly acid medium.

2. A process according to claim 1 wherein R1 and R2 are methyl.

3. A process according to claim 1 wherein said catalyst is selected from the group consisting of platinum, palladium, rhodium, cobalt polysulfide or Raney nickel.

4. A process according to claim 3 wherein said catalyst is cobalt polysulfide or platinum.

5. A process according to claim 1 wherein the weakly acid medium contains acetic acid.

* * * * *